United States Patent [19]

Tachibana et al.

[11] Patent Number: 5,007,438
[45] Date of Patent: Apr. 16, 1991

[54] ENDERMIC APPLICATION KITS FOR EXTERNAL MEDICINES

[75] Inventors: Shunro Tachibana, 1-6-18, Kusagae, Chuo-ku, Fukuoka-shi, Fukuoka-ken; Uichi Shibata, Tokyo, both of Japan

[73] Assignees: Shunro Tachibana, Fukuoka; Meiji Seika Kaisha, Ltd., Tokyo, both of Japan

[21] Appl. No.: 329,914

[22] Filed: Mar. 28, 1989

Related U.S. Application Data

[62] Division of Ser. No. 120,555, Nov. 13, 1987, Pat. No. 4,821,740.

[30] Foreign Application Priority Data

Nov. 26, 1986 [JP] Japan .............................. 61-282703

[51] Int. Cl.$^5$ .............................................. A61N 1/00
[52] U.S. Cl. ..................................... 128/798; 604/20; 604/290
[58] Field of Search ................. 128/649, 798; 604/20, 604/290, 304, 307, 896

[56] References Cited

U.S. PATENT DOCUMENTS

| 4,309,989 | 1/1982 | Fahim | 604/290 |
| 4,640,689 | 2/1987 | Sibalis | 128/798 |
| 4,646,754 | 3/1987 | Seale | 128/649 |
| 4,657,543 | 4/1987 | Langer et al. | 604/290 |
| 4,702,732 | 10/1987 | Powers et al. | 128/798 |
| 4,708,716 | 11/1987 | Sibalis | 604/20 |
| 4,767,402 | 8/1988 | Kost et al. | 604/290 |

Primary Examiner—Max Hindenburg
Attorney, Agent, or Firm—Jordan and Hamburg

[57] ABSTRACT

Disclosed is an endermic application kit for external medicines, which comprises a drug-containing layer as provided near an ultrasonic oscillator. The kit includes a cylindrical fixed-type or portable-type and a flat regular-type or adhesive-type, and the adhesive-type may be flexible and elastic. The drug absorption is ensured by the action of the ultrasonic waves from the oscillator and the drug release can be controlled by varying the ultrasonic wave output from the oscillator.

22 Claims, 2 Drawing Sheets

FIG. 1
FIG. 3
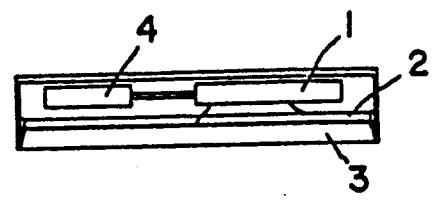
FIG. 4a
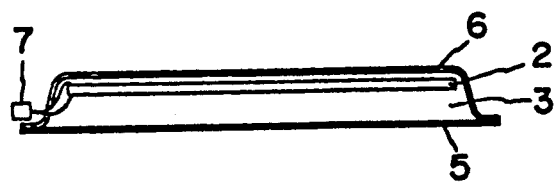
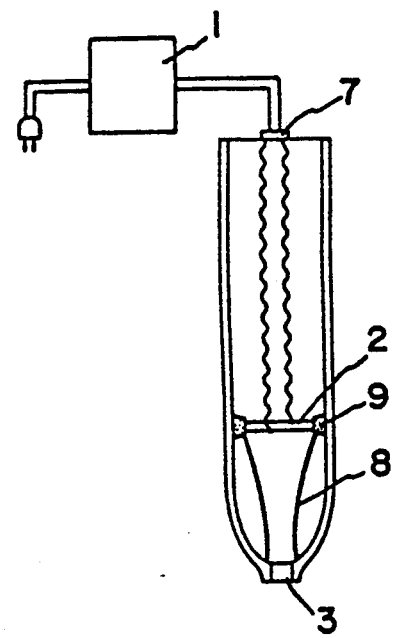
FIG. 2
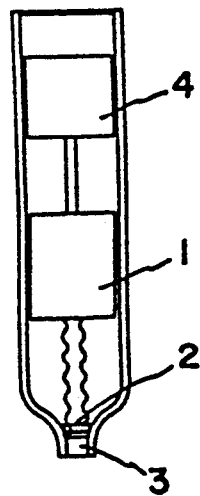
FIG. 4b
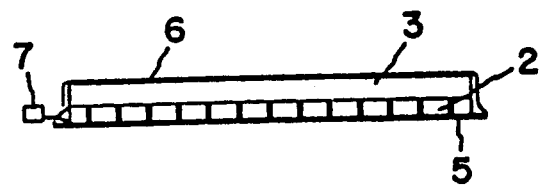

ENDERMIC APPLICATION KITS FOR EXTERNAL MEDICINES

This is a division of application Ser. No. 120,555 filed Nov. 13, 1987, now U.S. Pat. No. 4,821,740.

FIELD OF THE INVENTION

The present invention relates to endermic application kits for external medicines, with which drugs can be administered into a human body through the skin thereof with high absorption efficiency by the utilization of the function of ultrasonic oscillation.

BACKGROUND OF THE INVENTION

Means for administration of medicines to human bodies for remedy and prevention of human diseases include a method of peroral or parenteral administration by the use of an injection, a pill, a capsule, a suppository, etc. and a method of endermic administration by the use of an ointment, a drug-containing adhesive plaster, etc. Among them, the endermic administration method has almost been disregarded up to the present except the direct application of external medicines, since the endermic absorption of a drug is extremely low. (This is especially because a skin physiologically has a biological barrier function against microorganisms, chemical substances, radioactive substances, heat, etc.) Recently, however, various external medicines for endermic application are being developed through recent progress of pharmaceutical technique.

In the conventional drug-administration method by the use of peroral medicines, injections, suppositories, etc., in general, the drug concentration rapidly achieves its peak and then decreases with the lapse of time, and therefore, it is difficult to maintain a constant concentration of the drug in the blood. Even the most conventional peroral medicines have various difficult problems including the induction of gastroenteric disorders, the inactivation of the drug during the initial passage through liver after the absorption thereof from the intestine, the induction of hepatopathy, etc., and the drugs which may fully satisfy the conditions for use as a medicine are extremely limitative. In addition, the injection also has various difficult problems including the use of a needle, the induction of immunoreaction which would be caused by the direct injection of a foreign substance, etc. Furthermore, this may bring on shock or the like dangerous state, since the removal of the drug once injected into a body by injection is almost impossible.

Under the circumstances, particular attention is recently being riveted to an endermic application method, which is free from the above-mentioned defects in the case of peroral or parenteral administration methods and which can maintain the relatively constant drug concentration in blood without any dangerous immunoreaction, and an ointment or a drug-containing adhesive plaster is used for the endermic application method.

In the endermic application method by the use of such ointment, drug-containing adhesive plaster or the like, the drug is required to be transferred from the skin to the capillary bed. Since the possibility of the passage of the drug through the corneal layer or keratin layer of epidermis depends upon the various properties of the drug, including the oil-solubility, the water-solubility, the drug concentration, the pH value, the molecular weight, etc., it was difficult to maintain the sufficient drug concentration in blood by the endermic administration method. In order to solve these difficult problems, a study on the base compositions for introducing the drug into the inside of the skin by means of chemical techniques has predominantly been carried out, which resulted in success of limited base compositions for only several kinds of medicines.

SUMMARY OF THE INVENTION

The present inventors earnestly studied so as to attain the possibility of facilitating the introduction of a drug into the inside of a skin by the utilization of a physical energy in such extent that would not traumatize the skin treated, so that the drug thus introduced can pass through the corneal layer or keratin layer of epidermis with high efficiency and that the drug concentration in blood can be sufficiently maintained, and as a result, have found that the application of a drug to the surface of a skin in the presence of an ultrasonic oscillation can lead to the remarkable introduction of the drug through the skin whereby the thus-introduced drug can be absorbed into the capillary bed to cause the elevation of the drug concentration in blood. On the basis of such an unexpected discovery, the present inventors have achieved the endermic application kits for external medicines of the present invention with high endermic availability.

Accordingly, the object of the present invention is to provide an endermic application kit for external medicines, which is characterized by the provision of a drug-containing layer near an ultrasonic oscillator.

BRIEF EXPLANATION OF DRAWINGS

FIG. 1 shows a cross-sectional view of a fixed-type endermic application kit of the present invention.

FIG. 2 shows a cross-sectional view of a portable-type endermic application kit of the present invention.

FIG. 3 shows a cross-sectional view of a regular-type endermic application kit of the present invention.

FIG. 4 (a) and (b) each show a cross-sectional view of an adhesive-type endermic application kit of the present invention.

Figure 5:
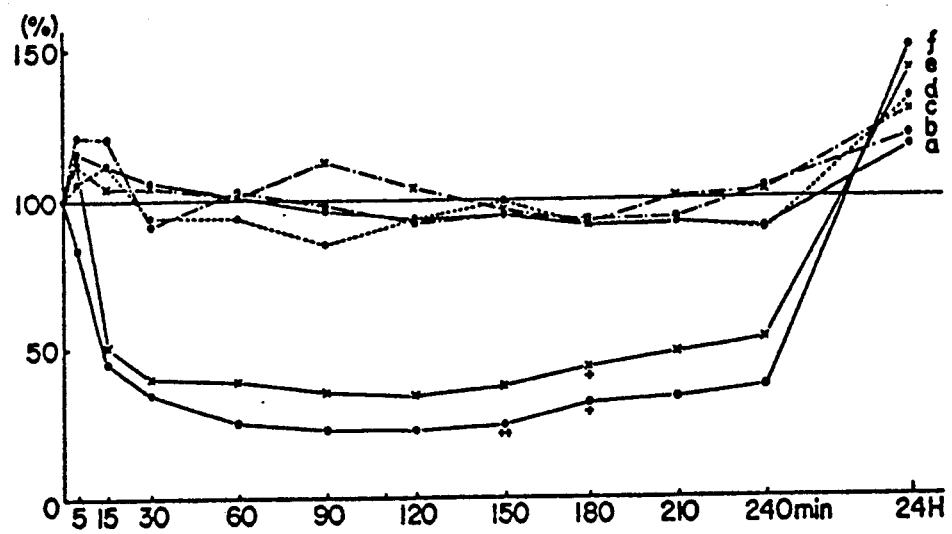
FIG. 5 is a graph to show the results of the absorption test No. 2 in which the endermic absorption of various drugs was tested in the presence of an ultrasonic oscillation.

In the drawings, (1) is an ultrasonic wave generator device, (2) an ultrasonic oscillator element, (3) a drug-containing layer, (4) a battery, (5) an adhesive layer, (6) a protective film, (7) a terminal, (8) an ultrasonic oscillation collector, and (9) a sponge-like buffer. The ultrasonic wave generating device and the ultrasonic oscillator element together constitute an ultrasonic oscillating means. The ultrasonic wave generating device 1 has a circuit which generates an electrical signal having an ultrasonic frequency and does not vibrate mechanically itself, while the ultrasonic oscillating element 2 receives the electrical signal from the ultrasonic wave generating device and mechanically vibrates.

In FIG. 5, (a) denotes the case of dipping in water only, (b) the case of dipping in water in the presence of an ultrasonic wave (5000 to 7000 Pa), (c) the case of dipping in water in the presence of an ultrasonic wave (3000 to 5000 Pa), (d) the case of dipping in 20 U/ml of insulin, (e) the case of dipping in 20 U/ml of insulin solution in the presence of an ultrasonic wave (3000 to 5000 Pa), and (f) the case of dipping in 20 U/ml of insulin solution in the presence of an ultrasonic wave (5000 to 7000 Pa).

Figure 6:
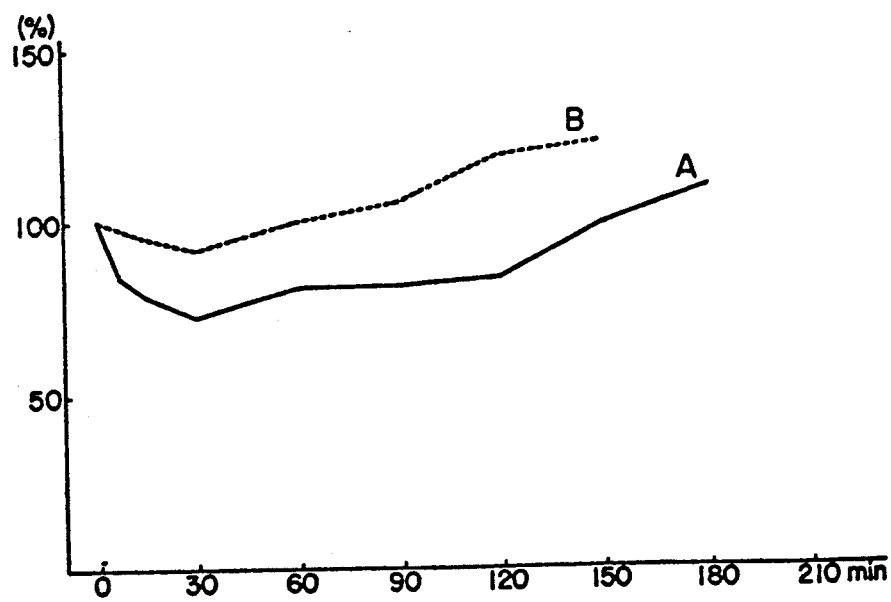
FIG. 6 is a graph to show the results of the absorption test in which the endermic absorption of a drug was tested by the use of the endermic application kit of the present invention.

In FIG. 6, (A) denotes the case of endermic application of an insulin gel in the presence of an ultrasonic wave (1750 Pa), and (B) the case of endermic application of an insulin gel in the absence of the ultrasonic wave.

DESCRIPTION OF THE INVENTION

By selecting the type of ultrasonic oscillating means and the electric power source, various endermic application kits can be adopted with the present invention, including fixed-type, portable-type, regular-type and adhesive-type kits, etc.

The ultrasonic oscillating means for use in the kits of the present invention is to be electrically insulated.

One embodiment of the fixed-type kit is shown in FIG. 1, where the ultrasonic wave generating device (1) as connected to a general alternating current source is connected to the ultrasonic oscillator element (2) as equipped in the bottom of the cylindrical container via the lead wires, and the drug-containing layer (3) is arranged at the top end of the container. In this type, a general electric source is used as the electric power, and therefore, a high energy can be applied to the kit. As the ultrasonic oscillator can be used a general ceramic oscillator, for example, made of barium titanate, zircon, lead titanate, etc.

The fixed-type kit of this kind is suitable for hospital or household use, which can be applied to a skin for a short period of time.

One embodiment of the portable-type kit is shown in FIG. 2, where the battery (4) and the ultrasonic wave generating device (1) as connected to the ultrasonic oscillator element (2) via the lead wires are housed in the cylindrical container, and the drug-containing layer (3) is arranged at the top end of the container. In this type, a battery is used as the electric power source, and therefore, a relatively high energy can be applied to the kit. The ultrasonic oscillator can be used with ceramic oscillator, like the above-mentioned fixed-type kit.

The portable-type kit of this kind is relatively small in size and compact and the electric source and the ultrasonic oscillator device are housed in one container, and therefore easy to carry for daily use. The portable-type kit can be used anywhere, when desired, by applying the same affected part on the skin thereby to administer the drug through the skin.

One embodiment of the regular-type kit is shown in FIG. 3, where the small battery (4) and the small-sized ultrasonic oscillator device such as IC oscillator device (1) as connected to the ultrasonic oscillator element (2) via the leading wires are housed in the flat container, and the drug-containing layer (3) is arranged below the ultrasonic oscillator element (2). In the kit of this type, both sides of the container are preferably provided with bands so that the drug-containing layer of the kit can usually be applied to the affected part of the skin by the function of these bands. Thus, the kit is especially suitably used for such diseases that require continuous administration of drugs.

One embodiment of the adhesive-type kit is shown in FIG. 4(a), where the drug-containing layer (3) is provided below the disc-like ceramic ultrasonic oscillator element (2), with laminating the drug-permeable adhesive layer (5) below the said layer (3), and the whole is covered with a plastic cover. The oscillator element (2) has the terminal (7) to be connected to an external wave generating device (1). In case the adhesive-type kit is required to be flexible or elastic, another embodiment is provided as shown in FIG. 4(b), in which the drug-containing layer (3) is provided on the flexible ultrasonic oscillator such as ultrasonic oscillator film (2), with laminating the drug-permeable adhesive layer (5) below the said film (2). The flexible ultrasonic oscillator (2) has the terminal (7) to be connected to an external wave generating device (1). For the formation of the kit of this type, an oscillator device can be applied to the conventional disc-type or tape-type drug-containing adhesive plaster which has generally been used in these days. Accordingly, the release rate of the drug from the kit can be controlled by the decrease or increase of the output energy of the ultrasonic oscillation and thus the drug concentration in the blood can freely be varied. The terminal (7) can be connected to a variable oscillator device with the possibility of the free control of the drug release rate and the drug concentration in blood, and the said ultrasonic oscillator device can be connected to a battery or a general electric source, and thus, the drug-containing layer of the kit is applied to the skin while the ultrasonic oscillation is imparted thereto. The kit being thus constituted, is suitable for application to such diseases that require an exact adjustment of the drug concentration in blood. In addition, the kit being flexible or elastic, the absorption of the drug from a fairly broad skin area is possible. A self-exciting system can also be adopted for these endermic application kits, in place of the use of the oscillator device.

Various kinds of drugs which have heretofore been used for external application, such as for ointments or drug-containing adhesive plasters, can be used in the kits of the present invention, including various slow-release drugs such as scopolamine, nitroglycerin, indomethacin, ketoprophene, calpronium chloride, etc. In addition, other drugs which were difficult to use in the form of ointments or drug-containing adhesive plasters for endermic application in the past can be used in the kits of the present invention, including, for example, a high molecular insulin, various kinds of hormones, antibiotics, carcinostatics, depressors, etc. Accordingly, the continuous slow release of the said drugs is possible by the use of the kits of the present invention. Moreover, the kits of the present invention can suitably be used for administration of a hypertensor to serious and emergent state patients who are difficult to ensure the blood vessel.

The administration of drugs by the use of the kits of the present invention is an endermic application by a physical technique and is therefore free from the problems in the endermic application by a chemical technique which would be limited because of the solubility and size of the molecules of the drug to be administered. Accordingly, the utility value of the kits of the present invention is extremely high.

As mentioned above, in the use of the kit of the present invention, the drug can be applied to the skin while an ultrasonic oscillation is applied thereto, and therefore, the introduction of the drug into the skin is good and the endermic administration of the drug through the skin can be carried out with extremely high efficiency. In addition, the control of the drug concentration in blood can rapidly be carried out by the control of the release rate of the drug from the kit.

Two experiments No. 1 and No. 2 were carried out, where the endermic absorption of various drugs was tested in the presence of an ultrasonic oscillation. The results are shown hereinafter.

EXPERIMENT NO. 1

Experiment with calpronium chloride solution (MTB) for observation of the permeation-accelerating effect by ultrasonic oscillation to drug which is known to be adequate for endermic application:

Hairless mice were used as experiment animals. They were dipped in 0.5%, 1% or 2% MTB solution, whereupon no mice died even when dipped in the highest 2% solution for an unlimited long period of time. However, when the mice were dipped in the same MTB solution with the application of an ultrasonic oscillation of 48 kHz and 2000 Pa (Pa means Pascal unit) thereto, they died in 160 minutes in the 0.5% solution, in 39 minutes in the 1% solution, and in 15 minutes in the 2% solution. The results indicate the extreme reduction of the survival time in proportion to the increase of the concentration of the solution. In addition, when the ultrasonic oscillation was intensified three times up to 6000 Pa, the time to death was further reduced such that the mice died in 19 minutes when dipped in the 0.5% solution, in 11.5 minutes in the 1% solution, and in 7.6 minutes in the 2% solution. Accordingly, the results further indicate the acceleration of the endermic absorption of the drug with the increase of the output power of the ultrasonic waves.

EXPERIMENT NO. 2

Effect by the application of ultrasonic oscillation to drug which is known to be quite difficult in absorption from skin by endermic administration:

Hairless mice were used like the above-mentioned Experiment No. 1 and the endermic application of insulin to the same mice was tried. The determination of the insulin absorption effect was carried out by the use of a dextrometer and the tail venous blood was measured for the determination. The mice were dipped in a 20 U/ml aqueous-insulin solution (novoactorapit MC) for 5 minutes while an ultrasonic oscillation was imparted thereto. After taken out from the solution, the state of the decrease of the blood sugar value of the thus dipped mice was observed for 240 minutes so as to evaluate the insulin effect by the endermic application of the insulin solution for 5 minutes. As control, mice were dipped in the 20 U/ml aqueous-insulin solution for 5 minutes in the absence of the ultrasonic oscillation, or mice were dipped in an insulin-free water in the presence of an ultrasonic for 5 minutes. These control mice were also observed, after taken out from the solution, in the same manner as above, to obtain the blood sugar value variation up to 240 minutes. The results obtained are shown in FIG. 5.

The blood sugar variation curve obtained by the 5 minutes endermic absorption of the 20 U/ml insulin solution in the presence of the 3000 to 5000 Pa and 48 kHz ultrasonic oscillation was almost the same as that obtained by the intradermal injection of the same insulin solution in an amount of 4 U/kg. The blood sugar values in FIG. 5 are shown by the term of the percentage on the basis of the 100 percentage of the value just before the experiment.

In this experiment, mice which had been fasting for 8 hours were used, and these were fed after 16 hours. Accordingly, the blood sugar value of the tested mice after 24 hours was higher than the time at the beginning of the experiment.

EXPERIMENT NO. 3

Experiment with antibiotics ABPC ointment (ampicillin phthalidyle HCl ointment)

2 g of antibiotics ABPC (10%) ointment was applied to the shaved portion of rabbits which had been shaved on their backs (7x7 cm) with an electric shaver. They were treated by an ultrasonic oscillation (100 kHz, 5000 Pa) in 20 minutes after the application. Then, after 20 minutes without the ultrasonic oscillation, the second treatment by the ultrasonic oscillation for 20 minutes followed and the ointment was then removed. Afterwards, the blood of the rabbits was gathered in 0 minute, 20 minutes, 40 minutes, 60 minutes, 120 minutes, 180 minutes, 240 minutes and 24 hours intervals, and the concentration ($\mu$g/ml) of ABPC in the blood was evaluated.

Furthermore, using the same animals to which only ABPC applied without the treatment by the ultrasonic oscillation, the concentration of ABPC in the blood of the experimented animals (untreated) was evaluated. The results are shown in the following table 1.

TABLE 1

| time | unit: $\mu$g/ml treated by the ultrasonic oscillation | untreated |
| --- | --- | --- |
| 0 (minutes) | 0 | 0 |
| 20 | 0.10 | 1.19 |
| 40 | 4.50 | 0.30 |
| 60 | 2.84 | 0.48 |
| 120 | 0.41 | 0.33 |
| 180 | 0.46 | 0.25 |
| 240 | 1.41 | 0.71 |
| 24 (hours) | 0.24 | 0.19 |

As apparent from the results shown above, with the treatment by the ultrasonic oscillation, the concentration in the blood peaked 40 minutes after the application; the amount of absorption was four times greater than those untreated by comparison.

EXPERIMENT NO. 4

Experiment with ethyl loflazepate (EL) ointment tranquilizer belonging to benzo diagepine group (1)

The five rats were employed in this experiment and had their back shaved with an electric shaver. 0.3 g of EL (5%) ointment (100 mg/kg approximately) was applied to the shaved portion of the back of each rat.

Each rat was treated as follows:

A. After application of the ointment and the ultrasonic oscillation treatment for 10 minutes, the blood was gathered in one hour.

B. After application of the ointment and the ultrasonic oscillation treatment for 20 minutes, the blood was gathered in one hour.

C. After application of the ointment and without the ultrasonic oscillation treatment, the blood was gathered in three hours.

D. After application of the ointment without the ultrasonic oscillation treatment, the blood was gathered in one hour.

Metabolic concentration of EL in serums in the gathered blood of the rats was evaluated.

The ultrasonic oscillation treatment was carried out in 100 KHZ, 2000 Pa with the ceramic oscillator (diameter: 20 mm) on the ointment.

The results were shown in Table 2.

TABLE 2

| Samples | Metabolic concentration of EL in serums (ng/ml) |
| --- | --- |
| A | 18.8 |
| B | 28.2 |
| C | 3.0 |
| D | 1.0 |

As apparent from the results shown above, with the treatment by the ultrasonic oscillation, the amount of absorption was eighteen times greater than those untreated when treated for 10 minutes and twenty-eight times greater when for 20 minutes.

EXPERIMENT NO. 5

Experiment with EL ointment (2)

2 g of EL ointment was applied to inner sides of the rabbits' ears. They were treated by the ultrasonic oscillation (100 kHz, 6000 Pa) in 10 minutes after the application. Then, after 10 minutes without the ultrasonic oscillation, the second treatment by the ultrasonic oscillation for 10 minutes followed and the ointment was then removed. Afterwards, the blood of the rabbits was gathered from the other side of the respective ear in 105 minutes and 265 minutes intervals, and the metabolic concentration of EL in the blood was evaluated.

Furthermore, as contrast, using the same animals from which the ointment was removed 30 minutes after application without the treatment by the ultrasonic oscillation, the concentration of EL in the blood of the experimented animals (untreated) was evaluated in 120 minutes and 290 minutes intervals. The results are shown in the following table 3.

| treated by the ultrasonic oscillation | | untreated | |
| --- | --- | --- | --- |
| time (minute) | concentration in the blood (ng/ml) | time (minute) | concentration in the blood (ng/ml) |
| 105 | 662.6 | 120 | 11.9 |
| 265 | 100.7 | 290 | 28.7 |

As apparent from the results shown above, the sufficient concentration of EL was evaluated such as 662.6 ng/ml with the treatment by ultrasonic oscillation although little amount of concentration such as 28.7 ng/ml in the absence of the treatment.

As mentioned above, it is apparent that the absorption of the drug into blood is improved when the endermic application of the drug is carried out in the presence of an ultrasonic oscillation.

The following examples are intended to illustrate the present invention but not to limit it in any way.

EXAMPLE 1

As shown in FIG. 1, this is a fixed-type endermic application kit for external medicines. In the cylindrical holder made of a synthetic resin, which has the drug-containing layer (3) at the top end thereof, the ceramic ultrasonic oscillator (2) is arranged above the drug-containing layer (3) via the bugle-shaped ultrasonic oscillation collector (8) by the aid of the holder inner wall and the sponge-like buffer (9), and the terminal (7) which is connected to the said oscillator (2) via the leading wires is provided at the other end of the holder. The terminal (7) is connected to the variable ultrasonic wave generating (1) to be connected to a general electric source in use.

EXAMPLE 2

As shown in FIG. 2, this is a portable-type endermic application kit for external medicines. In the pencil-shaped holder made of a synthetic resin, which has the drug-containing layer (3) at the top end thereof, the ceramic ultrasonic oscillator (2) is arranged on said drug-containing layer (3), and the ultrasonic wave generating device (1) is arranged above the said oscillator (2) and the battery (4) is further above the ultrasonic wave wave generating device (1), these parts being connected to each other via leading wires.

EXAMPLE 3

As shown in FIG. 3, this is a regular-type endermic application kit for external medicines. In the flat container made of a synthetic resin, which has the drug-containing layer (3) at the bottom thereof, the ceramic ultrasonic oscillator (2) is arranged on the said drug-containing layer (3), and the IC ultrasonic wave generating device (1) and the battery (4) are arranged in parallel above the said oscillator (2), these parts being connected to each via leading wires.

EXAMPLE 4

(a) As shown in FIG. 4(a), this is an adhesive-type endermic application kit for external medicines. The drug-containing layer (3) is arranged below the disc-like ceramic oscillator (2) having the terminal (7), and the drug-permeable adhesive layer (5) is laminated below the said layer (3), and the whole is covered with the protective film (6). The terminal (7) of this kit is connected to a variable ultrasonic wave generating device (1) to be connected to a general electric source in use.

(b) As shown in FIG. 4(b), this is an adhesive-type endermic application kit for external medicines. The drug-containing layer (3) is arranged on the flexible ultrasonic oscillator film (polyvinylidene fluoride film) (2) which has a number of pores, the terminal (7) being arranged at one side of the film, and the surface of the said layer (3) is covered with the protective film (6). In addition, the drug-permeable adhesive layer (5) is laminated below the said flexible ultrasonic oscillation film (2). The terminal (7) of this kit is connected to a variable ultrasonic oscillator device (1) to be connected to a general electric source in use.

Next, one experimental example to show the endermic absorption effect of the drug by the use of the kit of the present invention is described hereinafter.

EXPERIMENTAL EXAMPLE

Novoactorapit MC (40 U/ml purified neutral porcin insulin injection) was gelled with sodium polyacrylate, and the resulting gel was incorporated into the drug layer (3) of the kit of FIG. 4(a). The kit was applied to a Wistar rat at the groin (diameter: 15 mm) for 10 minutes, while an ultrasonic wave (1750 Pa, 20 kHz) was applied thereto for 5 minutes. Afterwards, the kit was removed and the variation of the blood sugar value of the tested rat was observed. As a control, the kit was applied to a control rat in the same manner for 120 minutes without the application of the ultrasonic wave thereto, and the variation of the blood sugar value was also observed. The results obtained are shown in FIG. 6.

The results apparently prove that in the case of the application of the kit of the present invention in the presence of the ultrasonic oscillation only for 5 minutes, the 25% blood sugar value depression lasted 120 minutes, and afterwards, the value gradually recovered to the original value in 180 minutes. On the contrary, in the case of the application of the same kit in the absence of the ultrasonic oscillation, the blood sugar value increased after having once somewhat decreased.

The effect of the present invention can be summarized as follows: According to the endermic application kits of the present invention, the drug as incorporated in the kit can surely be absorbed into the capillary bed through the surface of the skin, while the drug-release rate from the kit can be controlled by the control of the variation of the ultrasonic wave output from the kit. The endermic application kits of the present invention, which are characterized by such novel drug-delivery system, are advantageous for practical use.

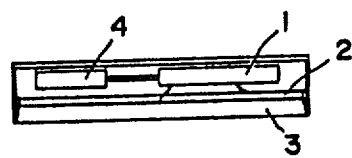
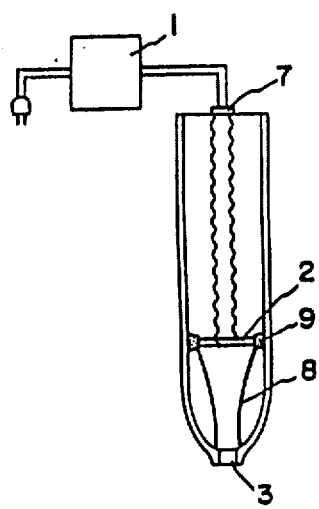
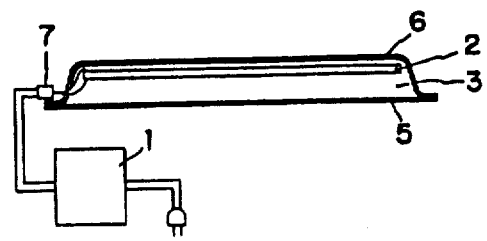
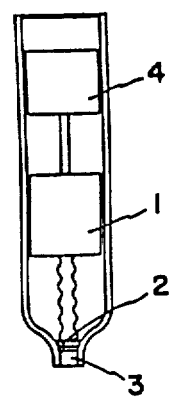
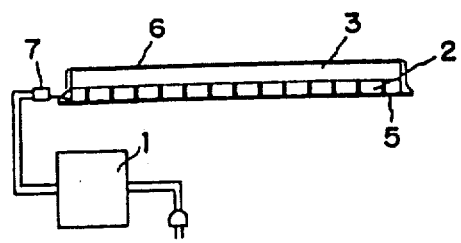

What is claimed is:

1. A device for administering medication to a host through the skin of the host comprising enclosure means, a layer of medication disposed within said enclosure means, and ultrasonic oscillating means comprising an ultrasonic oscillator element disposed in said enclosure means and operable to cause the medication within said layer of medication to pass from said enclosure means into said skin to thereby administer said medication to said host.

2. A device according to claim 1, wherein said ultrasonic oscillating means further comprises an ultrasonic wave generating means, and connecting means connecting said ultrasonic wave generating means to said ultrasonic oscillator element.

3. A device according to claim 2, wherein said ultrasonic wave generating means is disposed externally of said enclosure means.

4. A device according to claim 3, wherein said connecting means comprises lead wires passing through said enclosure means.

5. A device according to claim 2, wherein said ultrasonic wave generating means is disposed internally of said enclosure means.

6. A device according to claim 2, wherein said layer of medication, said ultrasonic oscillator element, and said ultrasonic wave generating means are disposed in superimposed array within said enclosure means.

7. A device according to claim 2, wherein said ultrasonic wave generating means further comprises a battery as a source of power, said battery being disposed within said enclosure means.

8. A device according to claim 2, wherein said ultrasonic wave generating means comprises an ultrasonic wave generating device and a battery, said ultrasonic wave generating device and said battery being disposed within said enclosure means.

9. A device according to claim 1, wherein said ultrasonic wave generating means is operable to vary the ultrasonic wave output energy to thereby control the rate of administration of said medication to said host.

10. A device according to claim 1, wherein said ultrasonic oscillator element is superimposed over said layer of medication such that said layer of medication is disposed between said ultrasonic oscillator element and said skin when said medication is being administered to said host.

11. A device according to claim 1, wherein said enclosure means comprises at least one portion made of a medication-permeable material being disposed between the medication in said layer of medication and said skin during administration of said medication such that said medication passes through said medication-permeable material to said skin.

12. A device according to claim 1, wherein said enclosure means comprises a cylindrical body having one longitudinal end portion at which said layer of medication is disposed, said ultrasonic oscillator element being disposed in said body in superimposed relationship over said layer of medication.

13. A device according to claim 1, wherein said ultrasonic oscillator element comprises a flexible material.

14. A device according to claim 1, wherein said enclosure means comprises a flexible material.

15. A device according to claim 1, wherein said ultrasonic oscillator element comprises a ceramic material.

16. A device according to claim 1, wherein said ultrasonic oscillator element is spaced from said layer of medication.

17. A device according to claim 1, wherein said ultrasonic oscillator element is disposed on said layer of medication.

18. A device according to claim 1 further comprising buffer means for supporting said ultrasonic oscillator element in said enclosure means.

19. A method for administering medication to a host through the skin of the host comprising the steps of disposing a layer of medication and an ultrasonic oscillator element within an enclosure, placing the enclosure in a position such that said layer of medication is juxtaposed to said skin, applying a source of ultrasonic wave energy to said ultrasonic oscillator element to thereby cause said medication to pass from said enclosure to said skin of said host to thereby effect administration of said medication to said host and controlling the rate of administration to said medication to said host by varying the output energy of said ultrasonic wave energy.

20. A method according to claim 19, wherein said enclosure is made at least partially of a medication-permeable layer, further comprising positioning said layer of medication on said skin such that said medication-permeable layer is disposed between said skin and said medication, and passing said medication through said medication-permeable layer to said skin.

21. A method for administering medication to a host through the skin of the host comprising the steps of disposing a layer of medication juxtaposed to said skin, superimposing an ultrasonic oscillator element over said layer of medication, applying ultrasonic wave energy to said ultrasonic oscillator element to thereby cause said medication to pass through said skin and controlling the rate of administration of said medication to said host by varying the output energy of said ultrasonic wave energy.

22. A device for administering medication to a host through the skin of the host comprising enclosure means, a layer of medication disposed within said enclosure means, an ultrasonic oscillator element disposed in said enclosure means, an ultrasonic wave generator disposed externally of said enclosure means, and lead wire means extending between said ultrasonic oscillator element and said ultrasonic wave generator, said ultrasonic oscillator element being operable to cause said medication within said layer of medication to pass from said enclosure means into said skin to thereby administer said medication to said host.

* * * * *

UNITED STATES PATENT AND TRADEMARK OFFICE
CERTIFICATE OF CORRECTION

PATENT NO. : 5,007,438

DATED : April 16, 1991

INVENTOR(S) : Shunro Tacibana et al.

It is certified that error appears in the above-identified patent and that said Letters Patent is hereby corrected as shown below:

ON TITLE PAGE: Item [45] before Patent date insert an asterisk [*]

After Item [73] add

[*] Notice: The portion of the term of this patent subsequent to April 18, 2006, has been disclaimed.

Signed and Sealed this

Tenth Day of March, 1992

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 5,007,438  
DATED : April 16, 1991  
INVENTOR(S) : Shunro Tachibana, et al It is certified that error appears in the above-indentified patent and that said Letters Patent is hereby corrected as shown below:

On the title page:

In the earlier Certificate of Correction dated March 10, 1992, under the heading "INVENTOR(S)" change "TACIBANA" to -- TACHIBANA --.

Correct Figs. 4a and 4b by adding the box 1 to each of these Figs. as shown in the attached copies of Figs. 4a and 4b.

Signed and Sealed this

Eighth Day of June, 1993

Attest:

MICHAEL K. KIRK

Attesting Officer     Acting Commissioner of Patents and Trademarks